(12) United States Patent
Owen

(10) Patent No.: US 7,927,864 B2
(45) Date of Patent: Apr. 19, 2011

(54) METHODS, KITS, AND COMPOSITIONS FOR DETECTING ENZYME ACTIVITY

(75) Inventor: John Owen, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 12/318,081

(22) Filed: Dec. 22, 2008

(65) Prior Publication Data
US 2009/0148851 A1 Jun. 11, 2009

Related U.S. Application Data

(63) Continuation of application No. 11/368,705, filed on Mar. 7, 2006, now Pat. No. 7,468,258.

(51) Int. Cl.
*C12M 1/34* (2006.01)
(52) U.S. Cl. .................................................. 435/287.1
(58) Field of Classification Search .................. None
See application file for complete search history.

(56) References Cited

U.S. PATENT DOCUMENTS
2007/0065895 A1 3/2007 Miyata et al.

OTHER PUBLICATIONS

Kokame et al. "FRETS-VWF73, a first fluorogenic substrate for ADAMTS13 assay", British Journal of Haematology, 2005, 129:93-100.*
Kruger et al. "An economical and preparative orthogonal solid phase synthesis of fluorescein and rhodamine derivatized peptides: FRET substrates for the *Staphylococcus aureus* sortase SrtA transpeptidase reation", Chem, Commun. 2002:2092-2093.*
Kokame et al. British Journal of Haematology 2005;129:93-100.
Zhang Biochem & Biophy Res Communication 2004, 323:674-678.
Zanardelli, et al., ADAMTS13 substrate recognition of von Willebrand factor A2 domain. J Biol Chem. Jan. 20, 2006;281 (3): 1555-63. Epub Oct. 12, 2005.
Sutherland, et al., Molecular modeling of the von Willebrand factor A2 Domain and the effects of associated type 2A von Willebrand disease mutations. J Mol Model. Aug. 2004;10(4):259-70. Epub Aug. 3, 2004.
Hassenpflug, et al., Impact of mutations in the von Willebrand factor A2 domain on ADAMTS13-dependent proteolysis. Blood. Mar. 15, 2006;107(6):2339-45. Epub Dec. 1, 2005.
Kokame, et al., VWF73, a region from D1596 to R1668 of von Willebrand factor, provides a minimal substrate for ADAMTS-13. Blood. Jan. 15, 2004;103(2):607-12. Epub Sep. 25, 2003.
Jenkins, et al., Molecular modeling of ligand and mutation sites of the type A domains of human von Willebrand factor and their relevance to von Willebrand's disease. Blood. Mar. 15, 1998;91(6):2032-44.
Dong, et al., ADAMTS-13 metalloprotease interacts with the endothelial cell-derived ultra-large von Willebrand factor. J Biol Chem. Aug. 8, 2003;278(32):29633-9. Epub May 29, 2003.
Anderson, et al., Zinc and calcium ions cooperatively modulate ADAMTS13 activity. J Biol Chem. Jan. 13, 2006;281 (2):850-7. Epub Nov. 11, 2005.
Majerus, et al., Binding of ADAMTS13 to von Willebrand factor. J Biol Chem. Jun. 10, 2005;280(23):21773-8. Epub Apr. 11, 2005.
Sheffield University VWF Information Homepage, including links to von Willebrand Factor mutations and polymorphisms associated with von Willebrand Diseases; Type 2A mutations: see http://www.ragtimedesign.com/vwf/mutation/mutationtableresults.php; Type 2A polymorphisms: http://www.ragtimedesign.com/vwf/polymorphism/polytableresults.php.

* cited by examiner

*Primary Examiner* — Karen Cochrane Carlson
*Assistant Examiner* — Bin Shen
(74) *Attorney, Agent, or Firm* — The Nath Law Group; Charles D. Niebylski; Joshua B. Goldberg

(57) ABSTRACT

The inventive subject matter relates to methods, kits, and compositions for detecting enzyme activity in a biological sample. In particular, the inventive subject matter relates to methods, kits, and compositions for detecting von Willebrand factor degrading enzyme activity in a biological sample.

8 Claims, 3 Drawing Sheets

METHODS, KITS, AND COMPOSITIONS FOR DETECTING ENZYME ACTIVITY

This application is a Continuation of U.S. patent application Ser. No. 11/368,705, filed Mar. 7, 2006, which issued on Dec. 23, 2008 as U.S. Pat. No. 7,468,258, the entire disclosure of which is incorporated herein by reference.

BACKGROUND OF THE INVENTIVE SUBJECT MATTER

1. Field of Inventive Subject Matter

The inventive subject matter relates to methods, kits, and compositions for detecting enzyme activity in a biological sample. In particular, the inventive subject matter relates to methods, kits, and compositions for detecting von Willebrand factor degrading enzyme activity in a biological sample.

2. Background

Proteases represent a number of families of proteolytic enzymes that catalytically hydrolyze peptide bonds. Principal groups of proteases include metalloproteases, serine proteases, cysteine proteases and aspartic proteases. Proteases, in particular serine proteases, are involved in a number of physiological processes such as blood coagulation, fertilization, inflammation, hormone production, the immune response and fibrinolysis.

Numerous disease states are caused, and can be characterized, by alterations in the activity of specific proteases and their inhibitors. For example emphysema, arthritis, thrombosis, cancer metastasis and some forms of hemophilia result from the lack of regulation of serine protease activities (see, for example, Textbook of Biochemistry with Clinical Correlations, John Wiley and Sons, Inc. N.Y. (1993)). In case of viral infection, the presence of viral proteases have been identified in infected cells. Such viral proteases include, for example, HIV protease associated with AIDS and NS3 protease associated with Hepatitis C. These viral proteases play a critical role in the virus life cycle.

Measurement of changes in the activity of a specific protease is clinically significant in the treatment and management of an underlying disease state. Proteases, however, are not generally easy to assay. Typical approaches include ELISA, using antibodies that bind the protease, or RIA, using various labeled substrates. Using natural substrates, assays are difficult to perform and expensive. With currently available synthetic substrates the assays are expensive, insensitive and nonselective. In addition, many "indicator" substrates require high quantities of protease which often results, in part, in the self destruction of the protease.

Recent approaches to protease detection rely on a cleavage-induced spectroscopic change in a departing chromogen or fluorogen located in the amino acid position on the carboxyl side of the cleavable peptide bond (see, for example U.S. Pat. Nos. 4,557,862 and 4,648,893). However, many proteases require two to as many as six amino acid residues on either side of the scissile bond for recognition of the protease. Thus, such approaches lack protease specificity.

Fluorogenic indicator compositions have been developed in which a "donor" fluorophore is joined to an "acceptor" chromophore by a short bridge containing a 7 amino acid peptide that is the binding site for an HIV protease and linkers joining the fluorophore and chromophore to the peptide (see, e.g., Wang, et al. (1990) Tetra. Letts. 45: 6493-6496). The signal of the donor fluorophore is quenched by the acceptor chromophore through a process believed to involve resonance energy transfer (RET). Cleavage of the peptide results in separation of the chromophore and fluorophore, removal of the quench, and generation of a subsequent signal measured from the donor fluorophore.

Unfortunately, the design of the bridge between the donor and the acceptor disclosed by Wang, et al. led to relatively inefficient quenching, limiting the sensitivity of the assay. In addition, the chromophore absorbed light in the ultraviolet range, reducing the sensitivity for detection in biological samples which typically contain molecules that absorb strongly in the ultraviolet.

More particularly, several types of assays currently exist for diagnosing VWF abnormalities. In the use of such assays, a VWF antigen must be determined for proper diagnosis. These assays variously include: radioimmunoassay ("RIA") involving competitive binding of radiolabeled antigen and unlabeled antigen to a high-affinity antibody; enzyme immunoassay ("EIA") and enzyme-linked immunosorbent assay ("ELISA"; see, e.g., U.S. Pat. No. 5,202,264) employing color reaction products of enzyme substrate interaction to measure antigen-antibody reaction; and latex immunoassay (LIA) utilizing antibodies bound at their $F^v$ region to latex particles and presenting a $F^{ab}$ region for interaction with antigens present in blood samples (see, e.g., U.S. Pat. No. 5,585,278).

The foregoing immunoassays are relatively simple and widely used, but suffer several disadvantages. The immunoassays require labeled antibodies, which can be quite expensive and entail intrinsic hazards when radioactive labels are used. In addition, the occurrence of non-specific binding of proteins to antigens, the formation of antibody complexes, and the presence of various types of commonly used solid supports, can each increase background noise and reduce sensitivity, resulting in false-positive determinations (see, e.g., Harlow, E., Antibodies: A Laboratory Manual, Cold Springs Harbor Laboratory 1988).

Clearly fluorogenic protease indicators that show a high signal level when cleaved, a low signal level when intact, that show a high degree of protease specificity, and that preferably function in the visible light range, are desirable. The inventive compositions, kits, and methods provide these and other benefits. Applicant has successfully produced a recombinant peptide that can be used as a substrate for enzyme activity assays, utilizing a recombinant polypeptide substrate as disclosed in greater detail herein.

SUMMARY OF THE INVENTIVE SUBJECT MATTER

ADAMTS13 is an exemplary metalloprotease that cleaves von Willebrand Factor (hereinafter "VWF"). ADAMTS13 deficiency is closely associated with both familial and acquired Thrombotic Thrombocytopenic Purpura (hereinafter "TTP"). Insufficient activity of this enzyme leads directly to accumulation of highly active multimers of VWF, which can cause massive aggregation of platelets and diffuse microvascular occlusion.

Current assay methods for TTP use full length VWF as a substrate and are very time consuming. There have been major efforts to develop facile quantitative assays which can be used on clinical plasma samples. Timely measurement of enzyme activity, such as ADAMTS13 activity relating to TTP, is expected to provide critical information for an early diagnosis of disorders such as TTP, and as a guide in treatment.

Thus, the present invention provides for novel reagents whose fluorescence increases in the presence of particular proteases. These fluorogenic protease indicators provide a high intensity fluorescent signal, preferably at a visible wavelength, when they are digested by a protease. Protease indicators that produce a high fluorescence signal in the visible wavelengths are particularly well suited for detection of protease activity in biological samples, in particular in liquid samples such as blood or plasma. The measurement can be carried out using a fluorescence microscope for histological samples and using a flow cytometer for cell suspension samples. Hence, the fluorogenic compositions of this invention allow detection of intracellular protease activity.

The inventive subject matter thus relates to a method for detecting the presence of von Willebrand factor degrading enzyme activity in a biological sample, comprising the steps of:
(a) mixing, in a suitable test medium, (1) the biological sample and (2) a polypeptide substrate comprising SEQ ID NO: 1, or an equivalent or homologue thereof,
wherein the substrate is labeled with two or more fluorophores of the same species, the two or more fluorophores exhibit fluorescence self-quenching in a full length substrate, and a fluorophore exhibits a detectable increase in fluorescence upon cleavage of the substrate by the von Willebrand factor degrading enzyme; and
(b) determining the presence of von Willebrand factor degrading enzyme activity from the presence, absence, or increase in fluorescence of a fluorophore.

The inventive subject matter further relates to a method for detecting the presence of ADAMTS13 activity in a biological sample, comprising the steps of:
(a) mixing, in a suitable test medium, (1) the biological sample and (2) a polypeptide substrate having an ADAMTS13 cleavage site and comprising SEQ ID NO: 1, or an equivalent or homologue thereof,
wherein the substrate is labeled with two fluorescein fluorophores at amino acid positions 4 and 16 of SEQ ID NO: 1, and there is a detectable increase in fluorescence upon cleavage of the substrate by ADAMTS13; and
(b) determining the presence of ADAMTS13 activity from the presence, absence, or increase in fluorescence.

In addition, the inventive subject matter relates to a kit for detecting the presence of von Willebrand factor degrading enzyme activity in a biological sample, comprising:
(a) a polypeptide substrate comprising SEQ ID NO: 1, or an equivalent or homologue thereof,
wherein the substrate is labeled with two or more fluorophores of the same species, the two or more fluorophores exhibit fluorescence self-quenching in a full length substrate, and a fluorophore exhibits a detectable increase in fluorescence upon cleavage of the substrate by the von Willebrand factor degrading enzyme; and
(b) a medium which is biologically suitable for permitting von Willebrand factor degrading enzyme activity.

Further, the inventive subject matter relates to a process for producing a FRET substrate, comprising the steps of:
(a) producing a modified DNA sequence which encodes an enzyme substrate, or a fragment thereof, by mutating one or more codons of the DNA sequence to encode at least two cysteine amino acids;
(b) expressing the modified DNA sequence to produce a modified substrate protein;
(c) collecting the modified substrate protein; and
(d) labeling each of the at least two cysteines in the modified protein with a fluorophore.

DETAILED DESCRIPTION OF THE INVENTIVE SUBJECT MATTER

Definitions

Figure 1:
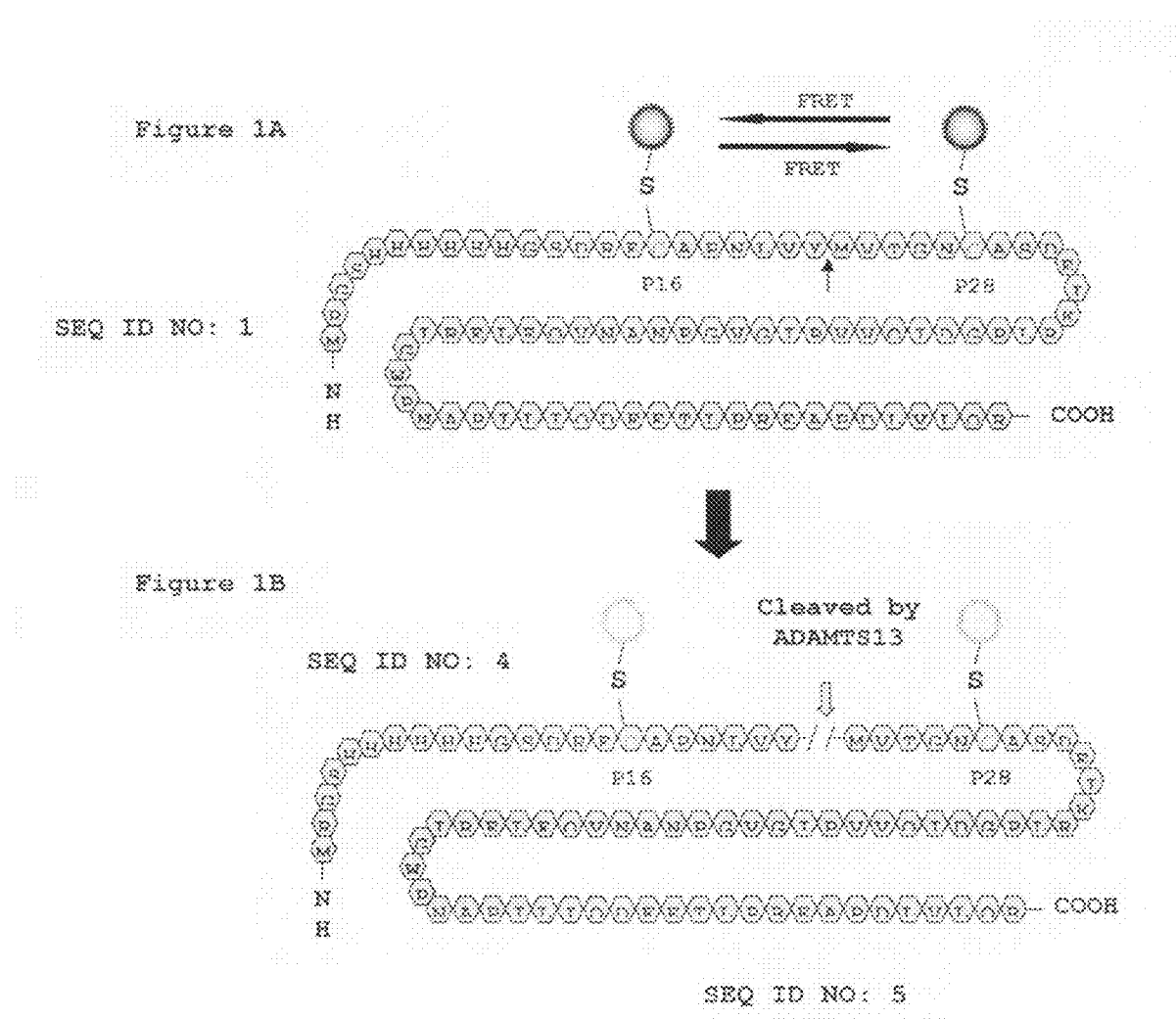
FIG. 1A is a drawing which depicts an exemplary recombinant substrate (SEQ ID NO: 1) labeled with homo-fluorophores which produce self-quenching in an un-cleaved state, according to one aspect of the inventive subject matter.
FIG. 1B is a drawing which depicts an exemplary recombinant substrate labeled with homo-fluorophores which produce fluorescence in a cleaved state (into SEQ ID NO: 4 and SEQ ID NO: 5), according to one aspect of the inventive subject matter.

The term "fluorescence resonance energy transfer" or "FRET" refers to an energy transfer mechanism between two fluorescent molecules without emission of a photon. A fluorescent donor is excited at its specific fluorescence excitation wavelength. By a long-range dipole-dipole coupling mechanism, this excited state is then nonradiatively transferred to a second molecule, the acceptor. The donor returns to the electronic ground state. The efficiency of FRET is dependent on the inverse sixth power of the intermolecular separation, making it useful over distances comparable with the dimensions of biological macromolecules. Thus, FRET is expected to be an important technique for investigating a variety of biological phenomena that produce changes in molecular proximity. When the donor and acceptor dyes are different, FRET can be detected by the appearance of sensitized fluorescence of the acceptor or by quenching of donor fluorescence. When the donor and acceptor are the same, FRET can be detected by fluorescence depolarization.

The term "detectable" refers to a change in a measurement which can be detected by instruments or methods which are known to skilled artisans.

The term "biological sample" refers to a sample obtained from an organism or from components (e.g., cells) of an organism.

The term "enzyme cleavage site" refers to an amino acid sequence that is characteristically recognized and cleaved by a protease. The enzyme cleavage site contains a peptide bond that is hydrolyzed by the protease and the amino acid residues joined by this peptide bond are said to form the cleavage site.

The term "fluorophore" refers to a molecule that absorbs light at a characteristic wavelength and then re-emits the light, most typically at a characteristic different wavelength. Fluorophores are well known to those of skill in the art and include, but are not limited to rhodamine and rhodamine derivatives, fluorescein and fluorescein derivatives, coumarins and chelators with the lanthanide ion series. A fluorophore is distinguished from a chromophore, which absorbs, but does not characteristically re-emit light.

The term "residue" or "amino acid" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

"Peptides" and "polypeptides" are chains of amino acids whose α carbons are linked through peptide bonds formed by a condensation reaction between the α carboxyl group of one amino acid and the amino group of another amino acid. The amino terminal amino acid at one end of the chain has a free amino group, while the carboxy terminal amino acid at the other end of the chain has a free carboxyl group.

Thus, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include peptide mimetics such as amino acids joined by an ether as opposed to an amide bond.

The term "domain" refers to a characteristic region of a polypeptide. The domain may be characterized by a particular structural feature such as a beta turn, an alpha helix, or a pleated sheet, by characteristic constituent amino acids (e.g. predominantly hydrophobic or hydrophilic amino acids, or repeating amino acid sequences), or by its localization in a particular region of the folded three dimensional polypeptide. As used herein, a region or domain is composed of a series of contiguous amino acids.

The term "protease activity" refers to the cleavage of a peptide by a protease. Protease activity of a particular protease may result in hydrolysis at particular peptide binding sites characteristically recognized by a particular protease. The particular protease may be characterized by the production of peptide fragments bearing particular terminal amino acid residues.

The amino acids referred to herein are at times described using a three-letter or a one-letter shorthand designation, as is well known in the art. The polypeptides described herein are written with the amino terminus at the left and the carboxyl terminus at the right. The amino acids comprising the peptide components of this invention may be numbered with respect to the protease cleavage site, with numbers increasing consecutively with distance in both the carboxyl and amino direction from the cleavage site.

The term "equivalent" as used herein in relation to the inventive compositions refers to a composition that performs substantially the same function as another composition in substantially the same way.

The term "homologue" as used herein in relation to the inventive compositions refers to a composition having an amino acid or nucleic acid sequence which corresponds or is similar to another composition in position, structure, and/or function. Homologous proteins should have at least 70% sequence homology, preferably at least 80% sequence homology, and most preferably at least 90% sequence homology. It is now well known to one of ordinary skill in the art that many proteins have identifiable functional domains, such as a substrate binding domain, a recognition sequence, or an active domain having, for example, a protease function. It is also well known, as discussed below, that substantially greater sequence variation is permitted in non-functional domains than functional domains, and thus sequence homology for purposes of this definition may be established over less than all of a protein sequence. Unless otherwise specifically described herein, Applicants hereby incorporate by reference the characteristics which are known in the art relating to particular proteins.

Further, the concept of sequence homology is tied to the distinction between conservative and non-conservative substitutions. In this regard, "identity" refers to a relationship between the sequences of two or more polypeptide molecules or two or more nucleic acid molecules, as determined by comparing the sequences thereof. In the art, "identity" also means the degree of sequence relatedness between nucleic acid molecules or polypeptides, as the case may be, as determined by the match between sequences of two or more nucleotides or two or more amino acids. "Identity" measures the percentage of identical matches between the smaller of two or more sequences with gap alignments (if any) addressed by a particular mathematical model, computer program, or algorithm.

The term "similarity" is used with regard to a related concept; in contrast to "identity," "similarity" refers to a measure of relatedness that includes both identical matches and conservative substitution matches. If two polypeptide sequences have, for example, 10/20 identical amino acids, and the remainder are all non-conservative substitutions, then the percentage identity and similarity would both be 50%. If in the same example, there are five more positions where there are conservative substitutions, then the percentage identity remains 50%, but the percentage similarity would be 75% (15/20). Therefore, in cases where there are conservative substitutions, the percentage similarity between two polypeptides will be higher than the percentage identity between those two polypeptides. For purposes of this application, Applicants consider conservative substitutions to be a "match" for purposes of determining percent homology.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. Such substituted residues may be introduced, for example, into non-homologous regions of a molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, e.g., Kyte, et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where a biologically functional protein is intended for use in embodiments involving protein-protein interactions, as disclosed herein. In certain embodiments, the greatest local average hydrophilicity of a protein, as governed by the hydrophilicity of its adjacent amino acids, correlates with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. One may also identify epitopes from primary amino acid sequences on the basis of hydrophilicity. Such regions are referred to as epitopic core regions, and in some embodiments correlate with a biological property of the protein.

Exemplary amino acid substitutions are set forth in the following Table A.

TABLE A

Amino Acid Substitution

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyricAcid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptides as set forth herein using well-known techniques. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues, in specific proteins or in similar proteins, that are important for activity or structure. In view of such a comparison, the skilled artisan can readily determine or predict the importance of amino acid residues in a protein that correspond to amino acid residues important for activity or structure in similar proteins. One skilled in the art may then opt for amino acid substitutions for such predicted important amino acid residues in order to maintain function.

One skilled in the art can also analyze the three-dimensional structure of a protein, and the amino acid sequence of the protein in relation to that structure. In view of such information, one skilled in the art may predict the alignment of amino acid residues of an protein with respect to its three-dimensional structure, or may determine three-dimensional structure experimentally. In certain embodiments, one skilled in the art may choose to not make radical changes to amino acid residues on the surface of the protein, since such residues may be involved in interactions with other molecules. Moreover, one skilled in the art may generate test variants, containing a single amino acid substitution at each desired amino acid residue which can be screened using activity assays known to those skilled in the art. Thus, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided, either alone or in combination with other mutations.

The Inventive Subject Matter

The inventive subject matter relates to methods, kits, and compositions for detecting enzyme activity in a biological sample. In particular, the inventive subject matter relates to methods, kits, and compositions for detecting von Willebrand factor degrading enzyme activity, i.e. protease activity, in a biological sample.

Proteases are enzymes that catalyze the breakdown of peptide bonds. They are essential to all physiologic and pathological processes. Measurement of protease activity is of great interest in research, drug discovery and development, and for use as diagnostic or prognostic markers in disease states. Some protease deficiencies are closely associated with certain disease conditions, such as alpha-1-Antitrypsin deficiency in Chronic Obstructive Pulmonary Disease, Antithrombin III deficiency in clotting disorders, and ADAMTS13 deficiency in thrombotic thrombocytopenic purpura.

Traditional Protease Assay Methods. Traditional protease assay methods involve multiple steps and are very time-consuming. Recently, fluorescence energy transfer (FRET) based protease assays have become popular. These assays eliminate gel electrophoresis, radioactivity, and the need for special skills or complicated instruments. They require only one step incubation and allow high throughput screening of a large number of samples.

Generation of pure, reliable, high quality substrate is essential to the development and improvement of such assays. Most FRET based assays use synthesized peptide substrates, the size of which is restricted by the limitations of chemical synthesis. These substrates are usually labeled with a pair of two different fluor-quencher molecules. However, when two identical fluorescent molecules are in close proximity, their fluorescence emission can also be quenched. This phenomenon of autoquenching has been widely used in protein structural studies and even in single-molecule structural studies, but has never been used to produce FRET substrates. Applicant has found that this mechanism can be applied to produce novel recombinant FRET substrates.

Von Willebrand Factor. Von Willebrand factor (VWF) is a polydispersed multimeric plasma glycoprotein circulating in plasma as a series of multimers ranging in size from about 500 to 20,000 kD, which participates in the initial platelet adhesion and transport of coagulation FVIII. Multimeric forms of VWF are composed of 250 kD polypeptide subunits linked together by disulfide bonds. The size distribution of vow multimers has a critical effect on its function, since the larger the VWF multimer, the more effective it is in promoting platelet adhesion.

VWF mediates the initial platelet adhesion to the subendothelium of the damaged vessel wall, only the larger multimers also exhibiting hemostatic activity. It is assumed that endothelial cells secret large polymeric forms of VWF and that those forms of VWF which have a low molecular weight (low molecular weight VWF) have arisen from proteolytic cleavage. The multimers having large molecular masses are stored in the Weibel-Pallade bodies of the endothelial cells and liberated upon stimulation. If ultra large multimers are present, spontaneous platelet aggregation and adhesion can occur and produce a thrombophilic state.

ADAMTS13. Recent studies have shown that A Disintegrin-like And Metalloprotease with ThromboSpondin type 1 motif ("ADAMTS13"), a proteolytic enzyme synthesized primarily in the liver, is responsible for proteolysis of VWF within its A2 domain. A deficiency of ADAMTS13 will result in the presence of uncleaved ultra large VWF multimers, a circumstance not commonly observed in normal plasma (see, e.g., Levy, G. G., et al. Nature 413:488-494 (2001)). Studies suggest that levels of activity and inhibition of this metalloprotease may be useful in the diagnosis and treatment of patients with thrombotic thrombocytopenia purpura (see, e.g., Mannucci P. et al. 98:2730-35 (2001)).

Thrombotic Thrombocytopenic Purpura. Thrombotic thrombocytopenic purpura (TTP) is an often rapidly fatal illness, first described by Moschowitz in 1924. It is characterized by anemia, a low platelet count (thrombocytopenia), and microvascular thrombosis. The anemia is caused by hemolysis and is associated with sharply pointed red cell fragments, termed schistocytes, that look as though they might have been sliced with a knife. The thrombocytopenia is caused by platelet deposition in thrombi, which leads to tissue damage that can produce renal failure, stroke, myocardial infarction, and acute respiratory distress. TTP often attacks otherwise healthy adults, with a preference for females of childbearing age. Without treatment the mortality rate exceeds 90%, but timely plasma exchange therapy has reduced the death rate significantly.

Until recently, the pathogenesis of TTP was obscure and the efficacy of plasma exchange therapy was unexplained. The thrombi in TTP are rich in platelets and von Willebrand factor (VWF) but relatively poor in fibrin, reflecting minimal participation of the classical blood clotting cascades. VWF is required for normal platelet adhesion, and exaggerated VWF adhesive activity has been proposed to cause TTP. Mutations in the metalloprotease that cleaves VWF, ADAMTS13, have been shown to cause a congenital form of TTP. There are several different manifestations of ADAMTS13 abnormalities resulting in TTP. In congenital TTP, ADAMTS13 is found to be quantitatively deficient. With acquired TTP, an IgG autoantibody is formed that inhibits ADAMTS13. In another form of "acquired TTP" more accurately known as hemolytic uremic syndrome ("HUS"), ADAMTS13 may be present in variable concentrations. For example, deficiencies of ADAMTS13 can result from *E. Coli* infections, veno-occlusive disease in bone marrow transplant, and a wide variety of drug toxicities.

Classically, the following five symptoms are indicative of TTP: fluctuating neurological symptoms, such as bizarre behavior, altered mental status, stroke or headaches; kidney failure; fever; thrombocytopenia, or low platelet count, leading to bruising or appearance of purpura; and microangiopathic hemolytic anemia.

Since the early 1990s, plasmapheresis has become the treatment of choice for TTP. This is the removal of the patient's blood plasma through apheresis and replacement with donor's plasma, either fresh frozen plasma or cryosupernatant. This procedure must be repeated daily to eliminate the inhibitor and ablate the symptoms. Lactate dehydrogenase levels have generally been used to monitor disease activity.

Many TTP patients need additional immunosuppressive therapy, with steroids such as prednisone, vincristine, cyclophosphamide, splenectomy or a combination of the above. Rituximab, a monoclonal antibody targeting B cells, has been successfully been used to treat patients with refractory disease. Approximately one-third of patients experiencing a TTP episode have a relapse within 10 years following their first attack.

While the mortality rate is very high for untreated cases, the prognosis is reasonably favorable, with 80-90% recovery for patients with idiopathic TTP diagnosed and treated early with plasmapheresis. Thus, there is a great need for early diagnosis and prompt treatment of TTP.

Applicant has found a highly effective assay for a defective VWF cleavage enzyme, kits for testing for a VWF cleavage enzyme, and a corresponding test for TTP. ADAMTS13 is a metalloproteinase that cleaves VWF between $Tyr^{1605}$ and $Met^{1606}$ of full length VWF. Full length VWF sequence is found, for example, in Accession Number AAB59458 and publications cited therein, the contents of which are publicly available and are hereby incorporated by reference in their entirety.

The smallest effective VWF-derived substrate is a 73 amino acid peptide from the VWF A2 domain. A recombinant 73 amino acid peptide was generated using a Qiagen pQE-100 His Tag vector and an M15 *E. coli* expression system. Two native amino acids, corresponding to full length Q1599 and P1611, that flank the ADAMTS13 cleavage site were mutated to cysteines. These two cysteines were subsequently labeled with fluorescein molecules.

The separation of these two fluorescein by ADAMTS13 cleavage generated measurable fluorescence increase. There was a steady increase of fluorescence over time during the incubation of this recombinant peptide with pooled normal plasma (PNP) used as the source of ADAMTS13. There was only minimal change in fluorescence during incubation with heat inactivated PNP and plasma samples from known TTP patients with absent ADAMTS13 activity. The enzyme kinetic assay yielded an excellent linear relationship between the rates of fluorescence increase and ADAMTS13 enzyme concentrations. Applicant has thus shown that fluorogenic recombinant peptides can be generated for FRET based protease assays.

Like many other enzymes, proteases may lose activity over time, especially when they are stored as their active forms. In addition, many proteases exist naturally in an inactive precursor form, which itself must be activated, for example, by hydrolysis of a particular peptide bond to produce the active form of the enzyme prior to use. Because the degree of activation is variable and because proteases may lose activity over time, it is often desirable to verify that the protease is active and to often quantify the activity before using a particular protease in a particular application. Thus, in one basic aspect of the inventive subject matter, fluorogenic molecules are used to assay the activity of purified protease made up as a reagent, e.g. in a buffer solution, for experimental or industrial use.

Previous approaches to verifying or quantifying protease activity involve combining an aliquot of the protease with its substrate, allowing a period of time for digestion to occur, and then measuring the amount of digested protein, most typically by HPLC. This approach is time consuming, utilizes expensive reagents, requires a number of steps and entails a considerable amount of labor. In contrast, the fluorogenic reagents of the present invention allow rapid determination of protease activity in a matter of minutes in a single-step procedure. An aliquot of the protease to be tested is simply added to, or contacted with, an inventive fluorogenic reagent and the subsequent change in fluorescence is monitored, e.g., using a fluorimeter or a fluorescence microplate reader.

In addition to determining protease activity in "reagent" solutions, the fluorogenic compositions of the present invention may be utilized to detect protease activity in biological samples. The sample may be of any biological tissue or fluid. Frequently the sample will be a "clinical sample" which is a sample derived from a patient. Such samples include, but are not limited to, sputum, blood, blood cells such as white blood cells, tissue or fine needle biopsy samples, urine, peritoneal fluid, and pleural fluid, or cells therefrom. Biological samples may also include sections of tissues such as frozen sections taken for histological purposes.

Inventive Methods

Thus, the inventive subject matter relates to a method for detecting the presence of von Willebrand factor degrading enzyme activity in a biological sample, comprising the steps of:

(a) mixing, in a suitable test medium, (1) the biological sample and (2) a polypeptide substrate comprising SEQ ID NO: 1, or an equivalent or homologue thereof,
wherein the substrate is labeled with two or more fluorophores of the same species, the two or more fluorophores exhibit fluorescence self-quenching in a full length substrate, and a fluorophore exhibits a detectable increase in fluorescence upon cleavage of the substrate by the von Willebrand factor degrading enzyme; and (b) determining the presence of von Willebrand factor degrading enzyme activity from the presence, absence, or increase in fluorescence of a fluorophore.

In one aspect of the inventive subject matter, the fluorophores comprise fluorescein, carboxytetramethylrhodamine, carboxyrhodamine-X, carboxyrhodamine 110, Alexa dyes, diethylaminocoumarin, or carbocyanine dyes.

In a preferred embodiment, the fluorophores comprise fluorescein.

In another aspect of the inventive subject matter, the substrate is labeled with two fluorophores.

In a preferred embodiment, a first labeled fluorophore comprises amino acid position 4 of SEQ ID NO: 1.

In another preferred embodiment, a second labeled fluorophore comprises amino acid position 16 of SEQ ID NO: 1.

In a more preferred embodiment, the two fluorophores flank a von Willebrand factor degrading enzyme cleavage site, each fluorophore-labeled amino acid is located within twelve amino acids of another fluorophore-labeled amino acid, and each fluorophore-labeled amino acid is located within eleven amino acids of the enzyme cleavage site.

In a further aspect of the inventive subject matter, the enzyme cleavage site comprises a tyrosine-methionine sequence at amino acid positions 10 and 11 of SEQ ID NO: 1.

In yet another aspect of the inventive subject matter, an amino acid of SEQ ID NO: 1 to be labeled with a fluorophore is substituted by cysteine.

In an alternate aspect of the inventive subject matter, the von Willebrand factor degrading enzyme is ADAMTS13.

In another preferred embodiment, the biological sample comprises blood or plasma. However, the sample may be of any biological tissue or fluid, such as sputum, blood, blood cells (e.g., white cells), tissue or fine needle biopsy samples, urine, peritoneal fluid, pleural fluid, sections of tissues such as frozen sections taken for histological purposes, or cells therefrom.

In particular, the inventive subject matter relates to a method for detecting the presence of ADAMTS13 activity in a biological sample, comprising the steps of:

(a) mixing, in a suitable test medium, (1) the biological sample and (2) a polypeptide substrate having an ADAMTS13 cleavage site and comprising SEQ ID NO: 1, or an equivalent or homologue thereof,
wherein the substrate is labeled with two fluorescein fluorophores at amino acid positions 4 and 16, and there is a detectable increase in fluorescence upon cleavage of the substrate by ADAMTS13; and (b) determining the presence of ADAMTS13 activity from the presence, absence, or increase in fluorescence.

In an alternate embodiment, the inventive methods may be utilized for diagnosing TTP in a patient. A method for diagnosing TTP in a patient comprises the steps of:

(a) mixing, in a suitable test medium, (1) a suitable biological sample collected from the patient and (2) a polypeptide substrate having an ADAMTS13 cleavage site and comprising SEQ ID NO: 1, or an equivalent or homologue thereof,
wherein the substrate is labeled with two fluorescein fluorophores at amino acid positions 4 and 16, and there is a detectable increase in fluorescence upon cleavage of the substrate by ADAMTS13; and (b) diagnosing likely TTP from below-normal or absent fluorescence of a fluorophore, in comparison to the fluorescence expected from an average sample, such as pooled normal plasma.

Inventive Kits

In addition, the inventive subject matter relates to a kit for detecting the presence of von Willebrand factor degrading enzyme activity in a biological sample, comprising:

(a) a polypeptide substrate comprising SEQ ID NO: 1, or an equivalent or homologue thereof,
wherein the substrate is labeled with two or more fluorophores of the same species, the two or more fluorophores exhibit fluorescence self-quenching in a full length substrate, and a fluorophore exhibits a detectable increase in fluorescence upon cleavage of the substrate by the von Willebrand factor degrading enzyme; and (b) a medium which is biologically suitable for permitting von Willebrand factor degrading enzyme activity.

In one aspect of the inventive subject matter, the fluorophores comprise fluorescein, carboxytetramethylrhodamine, carboxyrhodamine-X, carboxyrhodamine 110, Alexa dyes, diethylaminocoumarin, or carbocyanine dyes.

In a preferred embodiment, the fluorophores comprise fluorescein.

In another aspect of the inventive subject matter, the substrate is labeled with two fluorophores.

In a preferred embodiment, a first labeled fluorophore comprises amino acid position 4 of SEQ ID NO: 1.

In another preferred embodiment, a second labeled fluorophore comprises amino acid position 16 of SEQ ID NO: 1.

In a more preferred embodiment, the two fluorophores flank a von Willebrand factor degrading enzyme cleavage site, each fluorophore-labeled amino acid is located within twelve amino acids of another fluorophore-labeled amino acid, and each fluorophore-labeled amino acid is located within eleven amino acids of the enzyme cleavage site.

In a further aspect of the inventive subject matter, the enzyme cleavage site comprises a tyrosine-methionine sequence at amino acid positions 10 and 11 of SEQ ID NO: 1.

In an alternate aspect of the inventive subject matter, an amino acid of SEQ ID NO: 1 to be labeled with a fluorophore is substituted by cysteine.

Inventive Compositions

As discussed in greater detail above, Fluorescence Resonance Energy Transfer (FRET) is a technique for measuring interactions between proteins or protein domains in vitro or in vivo. In this technique, at least two fluorophores are fused to one or more protein(s) of interest. A characteristic excitation emission of a fluorophore is different when the fluorophores are in close proximity, as compared to when they are separated, allowing a determination of the state of fluorophore interaction, or lack thereof, based on the emission frequency and intensity.

One significant benefit of FRET technology is that it has excellent resolution. Because the efficiency falls off with the sixth power of the distance between molecules, FRET only occurs when the two fluorophores are within 20-100 μm (0.002-0.01 m) of each other, which means that the fluorophores must be brought together via intimate protein-protein interactions. Since biomolecules can be 50-200 μm in diameter, the position of the fluorophores within the protein complex is critical. If the fluorophores are over 200 μm apart while the proteins to which they are fused interact with each other, no signal is observed. Thus, FRET is an important technique for investigating a variety of biological phenomena that produce changes in molecular proximity. When FRET is used as a contrast mechanism, co-localization of proteins and other molecules can be imaged with spatial resolution beyond the limits of conventional optical microscopy. Thus, there is a need for FRET substrates which are, compared to current substrates, inexpensive, and relatively easy to make and use.

Thus, the inventive subject matter further relates to a process for producing a FRET substrate, comprising the steps of:

(a) producing a modified DNA sequence which encodes an enzyme substrate, or a fragment thereof, by mutating one or more codons of the DNA sequence to encode at least two cysteine amino acids;

(b) expressing the modified DNA sequence to produce a modified substrate protein;

(c) collecting the modified substrate protein; and (d) labeling each of the at least two cysteines in the modified protein with a fluorophore.

In one aspect of the inventive subject matter, the process further comprises:

(1) tagging the modified substrate protein; and
(2) purifying the tagged, modified substrate protein.

In another aspect of the inventive subject matter, the modified DNA sequence is produced by site-directed mutagenesis.

In a further aspect of the inventive subject matter the modified DNA sequence is expressed in vivo in a suitable host cell.

In an alternate aspect of the inventive subject matter, the modified DNA sequence is expressed in vitro in a suitable expression system.

In yet another aspect of the inventive subject matter, a cysteine amino acid is labeled with a fluorophore salt which conjugates to a free sulfhydryl group.

In a preferred embodiment, the fluorophore is fluorescein maleimide. Maleimide compounds are designed for facile conjugation to compounds which contain or have been modified to contain sulfhydryl groups. These reagents are pre-activated and may be coupled without further modification to any sulfhydryl containing compound. The maleimide/sulfhydryl interaction is highly specific, efficient and results in a stable thioether linkage. If conjugates are desired with a molecule that does not contain a sulfhydryl, one may be incorporated by a number of methods.

For example, compounds containing primary amines may be modified with S-acetylthioglycolic acid N-hydroxysuccinimide ester. This reagent will incorporate a protected sulfhydryl which may easily be deacetylated to allow for conjugation. In another example, disulfide bonds in the $F^c$ portion of antibodies may be reduced using 2-mercaptoethylamine. This generates two fragments containing free sulfhydryls which are distal from the antigen binding sites. Alternatively, free thiols may be generated by reducing disulfide bonds or by modifying other reactive groups such as primary amines with compounds like Traut's reagent, 2-iminothiolane.

In particular, fluorescein maleimide is designed for fluoresceinating proteins, nucleic acids or other molecules containing one or more thiol groups. Molecules to be labeled with fluorescein maleimide require a free thiol, or sulfhydryl, group. In the case of proteins, fluorescein maleimide will react with exposed cysteine residues. Specific labeling with fluorescein maleimide may be accomplished by limited reduction with dithiothreitol to free engineered cysteines. Once free thiol groups are available, labeling can be carried out as described in the Examples below.

In another preferred embodiment, the modified substrate protein is purified with an affinity column.

In a more preferred embodiment, the modified substrate protein is tagged with a poly-histidine tag and purified with a histidine affinity column.

General Synthesis of Inventive Compositions

The inventive compositions may be readily prepared by standard techniques of molecular biology, utilizing techniques known to those of ordinary skill in the art and in part as described in greater detail herein.

The products and intermediates may be isolated or purified using one or more standard purification techniques known to one of ordinary skill in the art, including, for example, one or more of simple solvent evaporation, recrystallization, distillation, sublimation, filtration, polymerase chain reaction, Southern blotting, Northern blotting, Western blotting, chromatography, including thin-layer chromatography, affinity chromatography, gel filtration chromatography, ion exchange chromatography, FPLC, HPLC (e.g. reverse phase HPLC), column chromatography, flash chromatography, radial chromatography, trituration, salt precipitation, two-phase separation, polymer precipitation, heat denaturation, isoelectric separation, dialysis, and the like.

EXAMPLES

The following examples are illustrative of the inventive subject matter and are not intended to be limitations thereon. Unless otherwise indicated, all percentages are based upon 100% by weight of the final composition.

Example 1

Exemplary Method for Preparation of Maleimide Compositions

1. Reconstitute a maleimide compound to 2-5 mg/ml in 0.15 M NaCl, 0.1 M Sodium phosphate pH 7.0. In order to promote efficient conjugation, the buffer should be deaerated and purged with nitrogen or argon before use. Also, the water used to prepare the buffer should be free of trace heavy metals and other oxidizing agents. The coupling may be performed in an amber vial to protect from light, which may catalyze oxidation as well.

2. Dissolve a sulfhydryl compound to be conjugated at 2-5 mg/ml in the same buffer used in step 1.

3. Stir gently for 3 hours at room temperature. Block any remaining maleimide groups by adding 1 M 2-mercaptoethanol to a final concentration of 0.0015 M. Stir for 15 minutes.

5. Block any remaining sulfhydryls by adding 0.3 M N-Ethylmaleimide in N,N-Dimethylformamide (DMF) to a final concentration of 0.003 M. However, it is known that some enzymes may lose activity if their native sulfhydryl groups are blocked. In this case, the sulfhydryl blocking step should be eliminated.

6. The conjugate can then be exchanged into the appropriate buffer by chromatography or dialysis to place it in the desired medium for use. For long term storage, the conjugate should be stored with 50% glycerol at −20° C.

7. For analysis purposes, approximately 5-10 g conjugate/ml will normally provide a sufficient signal for detection.

Example 2

Exemplary Protein Labeling with Fluorescein Maleimide

1. Dissolve the protein to be labeled in 100 mM phosphate buffer, pH 7.0 at a concentration of 5 mg/ml.

2. Dissolve a slight excess of the amount needed of fluorescein maleimide in dimethyl sulfoxide (DMSO) at a concentration of 20 mg/ml.

3. Add 251 fluorescein maleimide per ml of protein solution.

4. Incubate at room temperature for 3 hours with occasional stirring.

5. Separate the unreacted material from the protein by gel filtration or dialysis.

Example 3

Preparation of VWF Peptide Construct

A VWF73 DNA fragment was generated by PCR and inserted into His-tag pQE-100 vector using pQE-100-VWF-A2 constructs as templates. Using the QuikChange method, two native amino acid residues flanking the ADAMTS13 cleavage site were changed to Cysteines. As shown in FIG. 1A, the recombinant peptide substrate has two Cysteines labeled with fluorescein. When intact, because of the physical proximity, these two fluorogenic molecules absorb the fluorescent energy emitted from each other and fluorescence was quenched. Once cleaved by ADAMTS13 as shown in FIG. 1B, the fluorescence increases and this can be monitored using a fluorometer. Thus, it is apparent that two identical fluorescent molecules that flank an enzyme cleavage site can be labeled on a peptide substrate such that auto-quenching occurs.

Example 4

Production of Recombinant Peptide Substrate

Recombinant peptides were expressed in the *Escherichia coli* M15 strain. The His-tagged peptides were purified using HisTrap HP Nickel Sepharose column and labeled, on column, with Fluorescein Maleimide. The elution buffer was exchanged for 0.1% Trifluoroacetic acid and the peptide was recovered by vacuum drying.

Example 5

Measurement of ADAMTS13 Activity

The working peptide was prepared by dissolving the peptide pellets in DMSO and then diluted with assay buffer, 5 mM Bis-Tris, 25 mM $CaCl_2$, 0.005% Tween 20 at pH 6.0 to a final concentration of 4.5 μM. Pooled Normal Plasma (PNP) was used as a source of ADAMTS13. Heat inactivated PNP, heated overnight at 56° C., and known ADAMTS13-deficient patient plasma were used as negative controls. All samples were diluted 1 in 8 with assay buffer to reduce the ionic strength. Reactions were carried out in 96 well plates using 100 μL of dilute plasma and 100 μL of working peptide solution. The rate of fluorescence increase with time was monitored by a fluorometer.

Figure 2:
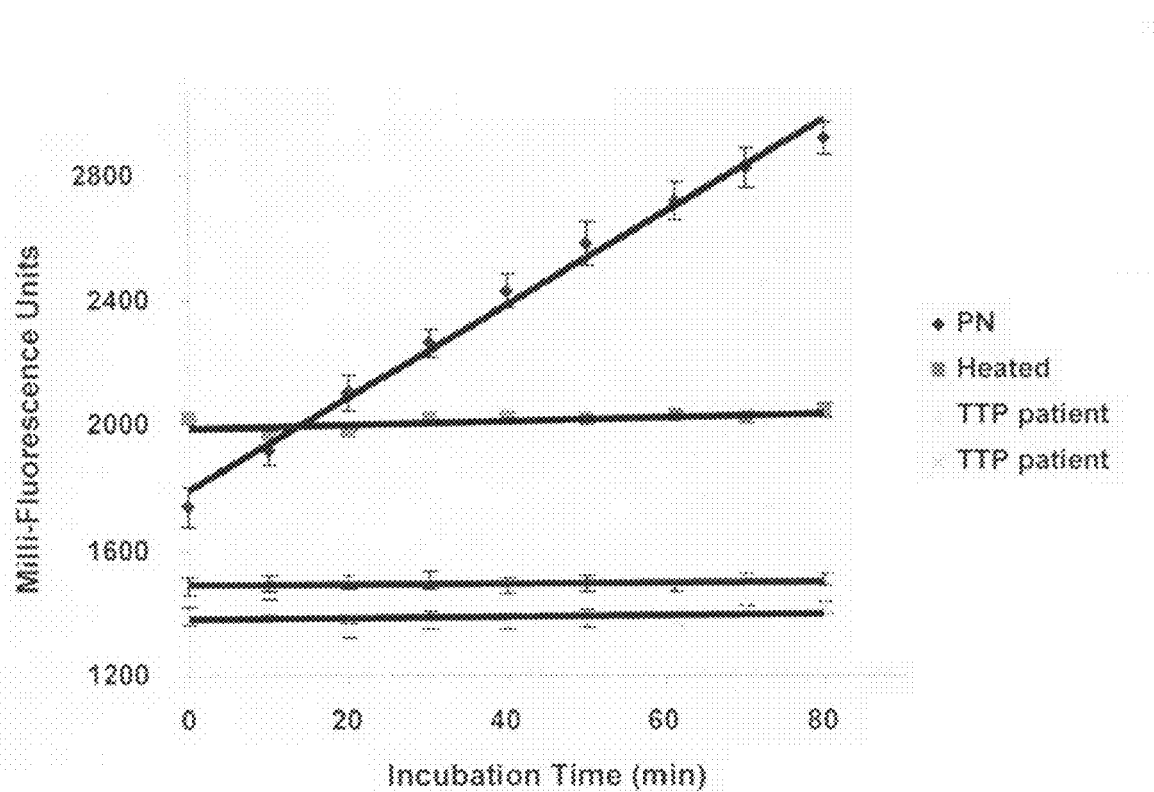
FIG. 2 is a graph which depicts the relationship between fluorescence intensity and time, measured for pooled normal plasma ("PN"), heat-inactivated PN ("heated"), and two TTP patient samples.

FIG. 2 depicts fluorescence of the recombinant peptide during incubation. With normal pooled plasma (PNP), there is steady increase of fluorescence over time. There is only minimal change in fluorescence during incubation with heat inactivated PNP and with two plasma samples from TTP patients with no ADAMTS13 activity. Each experiment was performed in triplicate and mean values are shown. Thus, it is apparent that the fluorescence increase resulting from the separation of fluors by ADAMTS13 cleavage of a labeled peptide substrate is measurable and can be used for FRET based enzyme assays.

Figure 3:
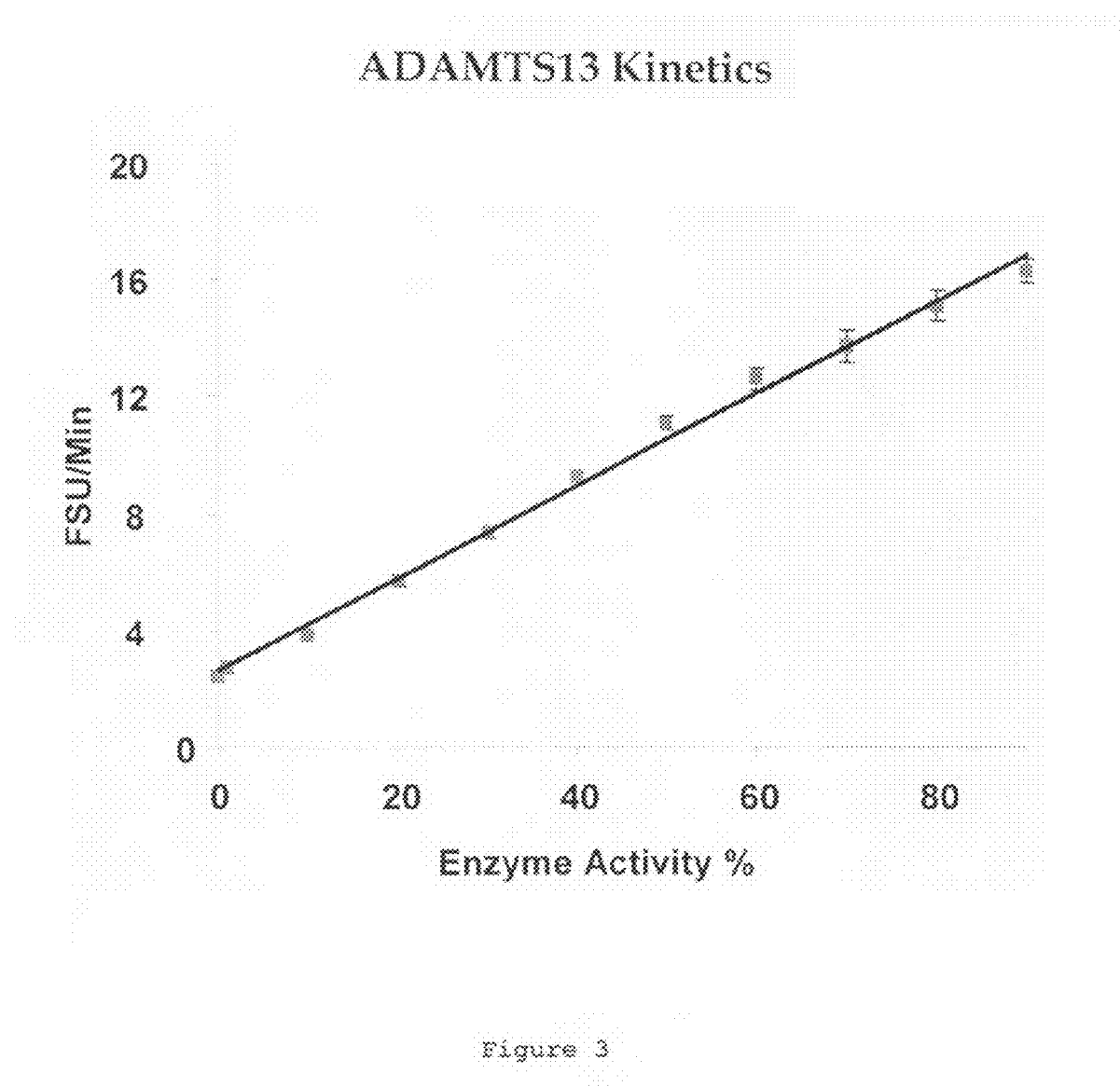
FIG. 3 is a graph which depicts the quantitative relationship between measured fluorescence intensity and percent enzyme activity.

FIG. 3 depicts the rates of change of fluorescence produced by dilutions of PNP in heat inactivated PNP. Undiluted PNP represents 100% ADAMTS13 enzyme activity for purposes of determining quantitative enzyme activity. Each point represents the mean±SEM of triplicate determination. A best fit straight line is shown in FIG. 3. Thus, it is apparent that recombinant fluorescein labeled peptides can be used as effective substrates in quantitative FRET based assays of ADAMTS13. Further techniques for quantitative analysis of enzyme activity are well known to skilled artisans.

The inventive subject matter being thus described, it will be obvious that the same may be modified or varied in many ways. Such modifications and variations are not to be regarded as a departure from the spirit and scope of the inventive subject matter and all such modifications and variations are intended to be included within the scope of the following claims.

I claim:

1. A kit for detecting the presence of von Willebrand factor degrading enzyme activity in a biological sample, comprising:
   (a) a polypeptide substrate consisting of SEQ ID NO: 1, or a polypeptide equivalent or homologue thereof, wherein the substrate is labeled with two or more fluorophores of the same species, the two or more fluorophores exhibit fluorescence self-quenching in a full length substrate, and a fluorophore exhibits a detectable increase in fluorescence upon cleavage of the substrate by the von Willebrand factor degrading enzyme; and
   (b) a medium which is biologically suitable for permitting von Willebrand factor degrading enzyme activity.

2. The kit of claim 1, wherein the fluorophores comprise fluorescein, carboxytetramethylrhodamine, carboxyrhodamine-X, carboxyrhodamine 110, Alexa dyes, diethylaminocoumarin, or carbocyanine dyes.

3. The kit of claim 2, wherein the fluorophores comprise fluorescein.

4. The kit of claim 1, wherein the substrate is labeled with two fluorophores.

5. The kit of claim 4, wherein a first labeled fluorophore comprises amino acid position 4 of SEQ ID NO: 1.

6. The kit of claim 4, wherein a second labeled fluorophore comprises amino acid position 16 of SEQ ID NO: 1.

7. The kit of claim 4, wherein the two fluorophores flank a von Willebrand factor degrading enzyme cleavage site, each fluorophore-labeled amino acid is located within twelve amino acids of another fluorophore-labeled amino acid, and each fluorophore-labeled amino acid is located within eleven amino acids of the enzyme cleavage site.

8. The kit of claim 1, wherein the enzyme cleavage site comprises a tyrosine-methionine sequence at amino acid positions 10 and 11 of SEQ ID NO: 1.

* * * * *

SEQUENCE LISTING

<160> NUMBER OF SEQ ID NOS: 5

<210> SEQ ID NO 1
<211> LENGTH: 73
<212> TYPE: PRT
<213> ORGANISM: Artificial sequence
<220> FEATURE:
<223> OTHER INFORMATION: This is a 73 amino acid fragment of native von
      Willebrand factor, substituted with cysteines at positions 4 and
      16.
<220> FEATURE:
<221> NAME/KEY: SITE
<222> LOCATION: (10)..(11)
<223> OTHER INFORMATION: There is an ADAMTS13 cleavage site located
      between positions 10 and 11.

<400> SEQUENCE: 1

Asp Arg Glu Cys Ala Pro Asn Leu Val Tyr Met Val Thr Gly Asn Cys
1               5                   10                  15

Ala Ser Asp Glu Ile Lys Arg Leu Pro Gly Asp Ile Gln Val Val Pro
            20                  25                  30

Ile Gly Val Gly Pro Asn Ala Asn Val Gln Glu Leu Glu Arg Ile Gly
        35                  40                  45

Trp Pro Asn Ala Pro Ile Leu Ile Gln Asp Phe Glu Thr Leu Pro Arg
    50                  55                  60

Glu Ala Pro Asp Leu Val Leu Gln Arg
65                  70

<210> SEQ ID NO 2
<211> LENGTH: 73
<212> TYPE: PRT
<213> ORGANISM: Artificial sequence
<220> FEATURE:
<223> OTHER INFORMATION: This is a 73 amino acid fragment of native von
      Willebrand factor.
<220> FEATURE:
<221> NAME/KEY: SITE
<222> LOCATION: (10)..(11)
<223> OTHER INFORMATION: There is an ADAMTS13 cleavage site located
      between positions 10 and 11.

<400> SEQUENCE: 2

Asp Arg Glu Gln Ala Pro Asn Leu Val Tyr Met Val Thr Gly Asn Pro
1               5                   10                  15

Ala Ser Asp Glu Ile Lys Arg Leu Pro Gly Asp Ile Gln Val Val Pro
            20                  25                  30

Ile Gly Val Gly Pro Asn Ala Asn Val Gln Glu Leu Glu Arg Ile Gly
        35                  40                  45

Trp Pro Asn Ala Pro Ile Leu Ile Gln Asp Phe Glu Thr Leu Pro Arg
    50                  55                  60

Glu Ala Pro Asp Leu Val Leu Gln Arg
65                  70

<210> SEQ ID NO 3
<211> LENGTH: 85
<212> TYPE: PRT
<213> ORGANISM: Artificial sequence
<220> FEATURE:
<223> OTHER INFORMATION: This is an 85 amino acid fragment of native von
      Willebrand factor, substituted with cysteines at positions 16 and
      28, and having a 12 amino acid leader sequence incorporating a
      poly-histidine region.
<220> FEATURE:
<221> NAME/KEY: SITE
<222> LOCATION: (22)..(23)

```
<223> OTHER INFORMATION: There is an ADAMTS13 cleavage site between
      positions 22 and 23.

<400> SEQUENCE: 3

Met Arg Gly Ser His His His His His Gly Ser Asp Arg Glu Cys
1               5                   10                  15

Ala Pro Asn Leu Val Tyr Met Val Thr Gly Asn Cys Ala Ser Asp Glu
            20                  25                  30

Ile Lys Arg Leu Pro Gly Asp Ile Gln Val Val Pro Ile Gly Val Gly
        35                  40                  45

Pro Asn Ala Asn Val Gln Glu Leu Glu Arg Ile Gly Trp Pro Asn Ala
    50                  55                  60

Pro Ile Leu Ile Gln Asp Phe Glu Thr Leu Pro Arg Glu Ala Pro Asp
65                  70                  75                  80

Leu Val Leu Gln Arg
                85

<210> SEQ ID NO 4
<211> LENGTH: 10
<212> TYPE: PRT
<213> ORGANISM: Artificial sequence
<220> FEATURE:
<223> OTHER INFORMATION: This is a first cleavage product of SEQ ID NO.
      1 cleaved with the ADAMTS13 enzyme.

<400> SEQUENCE: 4

Asp Arg Glu Cys Ala Pro Asn Leu Val Tyr
1               5                   10

<210> SEQ ID NO 5
<211> LENGTH: 63
<212> TYPE: PRT
<213> ORGANISM: Artificial sequence
<220> FEATURE:
<223> OTHER INFORMATION: This is a second cleavage product of SEQ ID NO.
      1 cleaved with the ADAMTS13 enzyme.

<400> SEQUENCE: 5

Met Val Thr Gly Asn Cys Ala Ser Asp Glu Ile Lys Arg Leu Pro Gly
1               5                   10                  15

Asp Ile Gln Val Val Pro Ile Gly Val Gly Pro Asn Ala Asn Val Gln
            20                  25                  30

Glu Leu Glu Arg Ile Gly Trp Pro Asn Ala Pro Ile Leu Ile Gln Asp
        35                  40                  45

Phe Glu Thr Leu Pro Arg Glu Ala Pro Asp Leu Val Leu Gln Arg
    50                  55                  60
```